US012533252B1

(12) United States Patent
Chetlapalli et al.

(10) Patent No.: US 12,533,252 B1
(45) Date of Patent: Jan. 27, 2026

(54) ELBOW BRACE WITH TWIST ADJUSTMENT

(71) Applicant: WEBER ORTHOPEDIC, L.P., Santa Paula, CA (US)

(72) Inventors: Janakiram Srinivasa Rao Chetlapalli, Frisco, TX (US); Jamie Mcmillan, Billings, MT (US); Jim Buckhout, Keller, TX (US)

(73) Assignee: Weber Orthopedic, L.P., DFW Airport, TX (US)

( * ) Notice: Subject to any disclaimer, the term of this patent is extended or adjusted under 35 U.S.C. 154(b) by 397 days.

(21) Appl. No.: 17/865,247

(22) Filed: Jul. 14, 2022

Related U.S. Application Data

(60) Provisional application No. 63/221,931, filed on Jul. 14, 2021.

(51) Int. Cl.
*A61F 5/01* (2006.01)

(52) U.S. Cl.
CPC ............ *A61F 5/0118* (2013.01); *A61F 5/013* (2013.01); *A61F 2005/0167* (2013.01)

(58) Field of Classification Search
CPC ........ A61F 5/0118; A61F 5/0102; A61F 5/01; A61F 2005/0167; A61F 2005/0165; A61F 2005/0132; A61F 5/013; A61F 5/373; A61F 5/05858; A61F 5/0123; A61F 5/0125; A61F 5/0585; A61F 5/05841; A61F 5/0106; A61F 5/0104; A61F 5/05866; A61F 5/37; A61F 5/3723
See application file for complete search history.

(56) References Cited

U.S. PATENT DOCUMENTS

| | | | | |
|---|---|---|---|---|
| 4,665,908 | A | 5/1987 | Calkin | |
| 7,156,819 | B2 | 1/2007 | Sieller et al. | |
| 7,806,842 | B2 | 10/2010 | Stevenson et al. | |
| 7,901,371 | B1 | 3/2011 | Vayntraub | |
| 7,954,204 | B2 | 6/2011 | Hammerslag et al. | |
| 10,098,774 | B2 * | 10/2018 | Modglin | A61F 5/01 |
| 10,231,859 | B1 * | 3/2019 | Thorne | A61H 1/024 |
| 10,743,621 | B2 | 8/2020 | Wyatt et al. | |
| 2006/0173391 | A1 | 8/2006 | Bodenschatz | |
| 2008/0066272 | A1 | 3/2008 | Hammerslag et al. | |
| 2008/0319362 | A1 | 12/2008 | Joseph | |
| 2016/0008157 | A1 * | 1/2016 | Brookover | A61F 5/0123 602/26 |
| 2024/0024145 | A1 * | 1/2024 | Johnson | A61F 5/0125 |

FOREIGN PATENT DOCUMENTS

| | | | | |
|---|---|---|---|---|
| EP | 589663 | A1 * | 3/1994 | A61F 5/013 |
| EP | 2964048 | B1 | 8/2019 | |

* cited by examiner

*Primary Examiner* — Victoria Hicks Fisher
(74) *Attorney, Agent, or Firm* — Paul Y. Feng; One LLP

(57) ABSTRACT

An orthopedic elbow brace having a forearm strut hinged to an upper arm strut, with two cuffs that are attached and slidable to the forearm strut, and a third cuff attached to the upper arm strut. First and second rotatable spools are positioned at the strut pivot. A lace, cable or wire interconnects the forearm and/or upper arm struts to the first spool, and another lace, cable or wire interconnects the forearm and/or upper arm struts to the second spool. Rotating the first and second spools tensions the laces, cables or wires to set an angular position between the forearm and upper arm struts corresponding to range of motion (ROM) limits for the brace. Attachment straps further secure the cuffs and the brace to the wearer's arm.

6 Claims, 8 Drawing Sheets

ELBOW BRACE WITH TWIST ADJUSTMENT

CROSS-REFERENCE TO RELATED APPLICATIONS

This non-provisional application claims benefit of priority from U.S. provisional application No. 63/221,931, filed Jul. 14, 2021, the contents of which are hereby incorporated by reference.

FIELD OF THE INVENTION

This present invention is directed to the field of medical devices for the treatment of disorders of the elbow.

BACKGROUND

The elbow is a hinged joint in a person's upper limb made up of three bones: the humerus in the upper arm, and the ulna and radius in the forearm. The ends of the bones are covered with cartilage. The function of the elbow joint is to extend and flex the arm for the hand to grasp and reach for objects. In most people, the range of motion in the elbow is from 0 degrees of elbow extension to 150 degrees of elbow flexion including everything in between those outer limits.

An injured elbow is often prone to stiffness, especially if immobilized for long periods of time during rehabilitation. Therefore, mobilization of the injured elbow must be started early. In the presence of injury to the ligaments, for example, the elbow joint must be protected to prevent these structures from being placed under tension during movement. Rehabilitation of the injured or post-surgical elbow includes the use of different types of elbow braces. They can have fixed articulation, or allow an adjustable range of motion (ROM) to restrict flexion-extension, for example.

Historically, ROM elbow brace development was derived from knee braces. As such, the elbow brace included two uprights hinged together, where each upright included two cuffs with associated straps. When installed, the two cuffs at the upper upright grip the wearer's upper arm with the straps tightly surrounding the humerus. The two cuffs at the lower upright grip the wearer's forearm with the straps surrounding the ulna and radius. This conventional elbow brace configuration attempts to achieve tight fitment of the brace to the limb yet allowing for the elbow to flex and extend to preserve the desired range of motion.

SUMMARY OF THE INVENTION

In a conventional elbow brace, the two upright hinged arrangement with four cuffed and strapped tight fitment to the wearer's arm is known to be inadequate, because the complex anatomical structure of the elbow in flexion and extension cannot be duplicated by a simple hinge. For example, with the hand in a supinated position, the ulna and radius are generally parallel; with the hand in a pronated position, the ulna and radius are crossed. Conventional elbow braces cannot accommodate for this complex motion. Further, the flexion versus extension in the elbow is more similar to the motion of a ball and socket rather than a simple hinge. Finally, the conventional brace to the limb attachment does not allow for smooth flexion and extension of the elbow joint, because the anatomical elbow joint needs allowance for an increase in length of the forearm arc.

Thus, flexion versus extension, and pronated versus supinated versus neutral hand positions cannot be effectively accommodated by a conventional elbow brace. As a result, that complex movement in the limb creates slippage of the conventional elbow brace from the limb. Once there is slippage or sloppy alignment of the brace to the arm, the rehabilitation efficacy of the conventional ROM elbow brace is severely diminished.

Therefore, various preferred embodiments of the present invention elbow brace are intended to adapt fitment of the elbow brace to more closely follow the complex movement of the elbow/arm through its range of motion. In a preferred embodiment, the present invention is directed to an orthopedic elbow brace, comprising an elongated forearm strut and an elongated upper arm strut; a strut pivot joining the forearm and upper arm struts together; first and second cuffs disposed on the forearm strut, wherein at least one of the first and second cuffs is slidable along the forearm strut. The brace includes a third cuff disposed on the upper arm strut where optionally at least two D-rings that may pivot and are disposed on the third cuff. The first and second cuffs attach to the wearer's forearm region. The third cuff attaches to the wearer's upper arm region.

In addition, first and second rotatable spools disposed on a common base plate are positioned proximate the strut pivot. A first lace, wire or cable or strand interconnects at least one of the forearm and upper arm struts to the first spool, and a second lace, wire, cable or strand interconnects at least one of the forearm and upper arm struts to the second spool, wherein rotating the first and second spools tensions the first and second laces to set an angular position between the forearm and upper arm struts corresponding to range of motion limits for the brace.

Preferably attachment straps disposed on the two D-rings pass around the upper arm, while attachment straps joint the first and second cuffs to attach the cuffs to the wearers forearm. The straps secure the elbow brace to the wearer's limb.

Optionally, the orthopedic elbow brace may have the lacing, wire, cable or strand threaded as follows: The first lace wraps around the first spool and interconnects with the forearm strut, and the second lace wraps around the second spool and interconnects with the upper arm strut. Alternatively, the first lace wraps around the first spool and interconnects with the forearm strut and the upper arm strut, and the second lace wraps around the second spool and interconnects with the forearm strut and the upper arm strut. Other lacing patterns are contemplated.

To further accommodate the complex elbow/arm movement, the preferred embodiment brace may include a forearm strut that has a longitudinal slot, and the first or second cuff includes a post that freely slides within that slot. The cuff or cuffs may slide longitudinally along the strut to automatically adjust for arm flexion or extension. Moreover, one or more of the first, second and third cuffs may optionally include an internal sleeve, wherein that sleeve is free to axially rotate inside the cuff. The cuff may further be hinged to the strut so it pivots relative to the length of the strut. The cuff rotation and/or pivoting is intended to accommodate the movement of the ulna and radius during supinated versus pronated hand positions of the wearer. Therefore, the preferred embodiment ROM elbow brace ensures joint mobility within the set limits of the ROM while allowing the limb to float within the closely fitted brace.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

Figure 1:
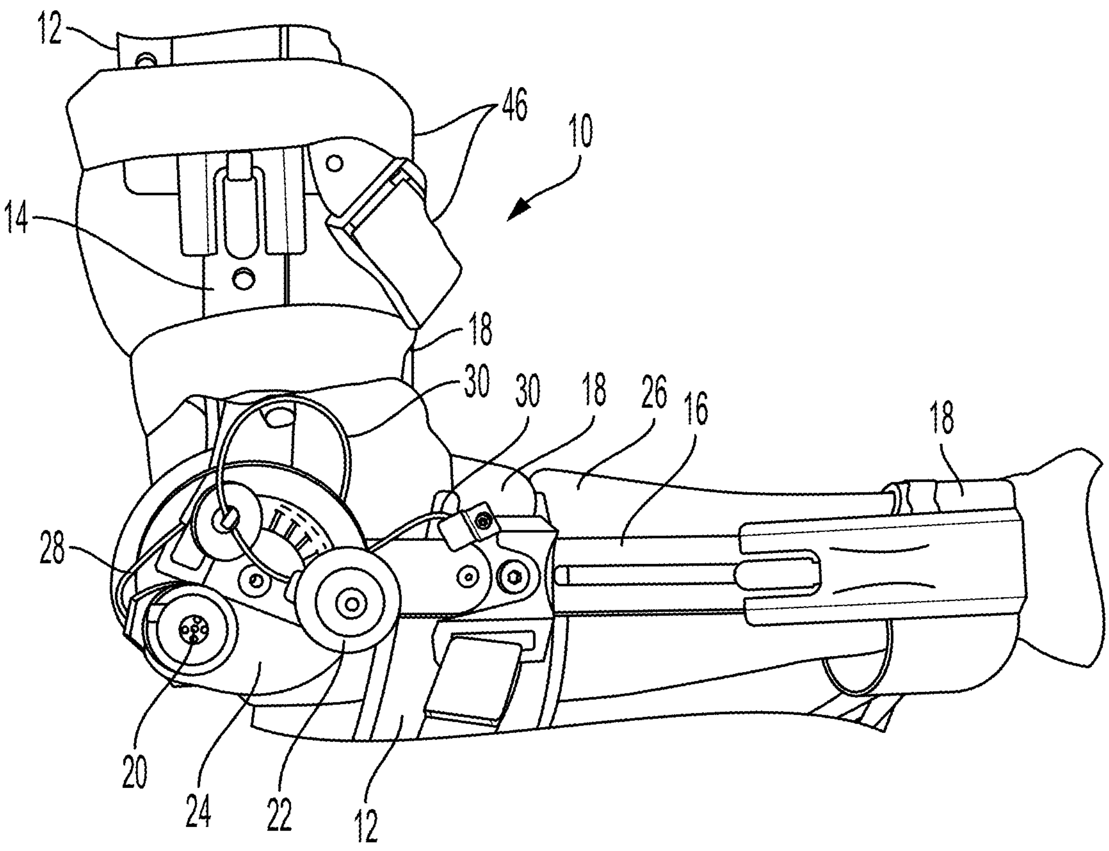
FIG. 1 is a side elevational view of a preferred embodiment elbow brace applied to an arm.

The present invention in a preferred embodiment is directed to an elbow brace 10 as shown worn on the right arm 26. The elbow brace 10 is held to the arm by one or more cuffs 12. Attachment straps 18 further help hold the elbow brace 10 to the arm 26. The brace 10 includes an upper arm strut 14 hinged to a forearm strut 16. First and second axially rotatable spools 20, 22 are mounted on a base plate 24, which plate is attached to the elbow brace. Each spool 20, 22 has its own lace 28, 30, joining the spool 20, 22 to the upper arm strut 14 and the forearm strut 16. Thus, rotating or twisting the spool 20, 22 tensions the laces 28, 30 thereby setting the angular limits for a range of motion (ROM) for the upper arm strut 14 and the forearm strut 16. Therefore, the wearer may freely move his or her arm within that controlled ROM, but not beyond those defined limits. The laces 28, 30 may be easily loosened by a reverse twist of one or both spools 20, 22 as the laces are coiled around each spool.

Each spool 20, 22 may include minute detents, click stops, or preferably friction twist lock to prevent unwanted rotation of the spool after the ROM is set. With a friction twist lock, the spools 20, 22 enable an infinite degree of ROM limit angles within the typical 0 degrees of elbow extension to 150 degrees of elbow flexion, versus a conventional elbow brace that have a center hinge gear tooth ROM limits defined by, say, 5 degree increments.

The laces 28, 30 are preferably made from a wire, strand, filament, cable and the like, with a single or multiple core, or twisted or braided strands. The laces exhibit low elasticity, and fabricated from aramid fiber, steel wire, braided plastic strands, polyester wire, or twisted fabric strands. When the wearer reaches either limit of the ROM, the laces provide a more cushioned stop as perceived by the wearer, versus metal stops in a conventional ROM elbow brace where the wearer feels a jarring impact when the extending or flexing arm runs into a hard ROM stop. The cushioned stops with the preferred embodiment spool-lace system is thus more gentle on the wearer's recovering elbow.

Figure 2:
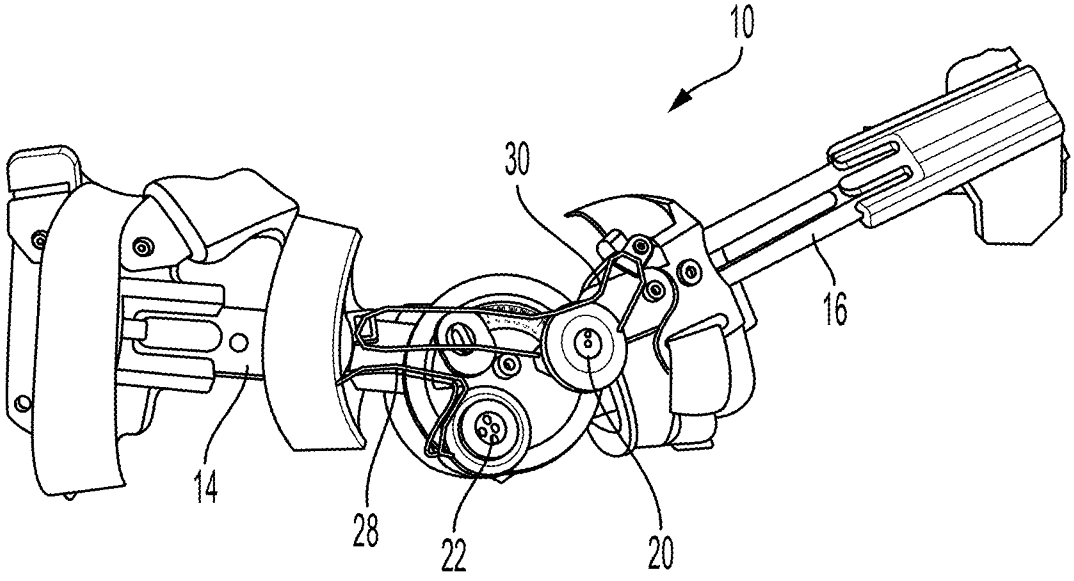
FIG. 2 is a side elevational view of the elbow brace from FIG. 1 with a preferred lacing pattern.
Figure 3:
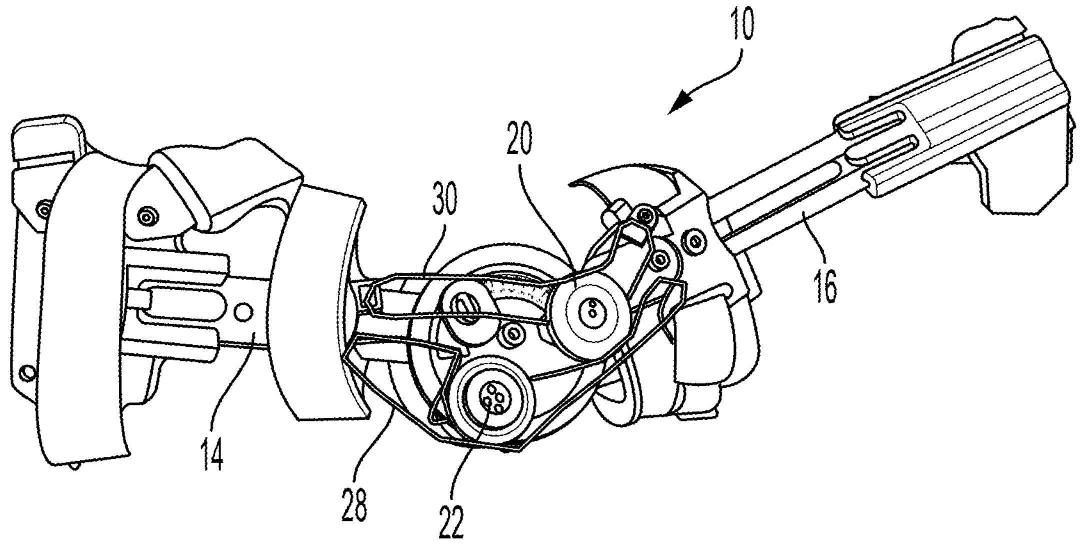
FIG. 3 is a side elevational view of the elbow brace from FIG. 1 with another preferred lacing pattern.

FIGS. 2 and 3 show two exemplary threading patterns for the laces 28, 30. FIG. 2 shows lace 30 looped to the upper arm strut 14 and the forearm strut 16 where both ends of lace 30 then tied to spool 20. The second lace 28 has one end tied to the upper arm strut 14 and the other end ties to the spool 22. FIG. 3 shows lace 30 looped around the upper arm strut 14 and forearm strut 16 with both ends tied at the spool 20. Lace 28 is also looped around the upper arm strut 14 and forearm strut 16 with both ends tied at spool 22. Other lacing patterns are contemplated. The laces may be anchored to the strut or there may be a guide with a groove or eyelet to allow the lace to slide through it spending on embodiment. In most embodiments, the laces will be in tension when the ROM limit is reached and may become slack when the arm is freely moving within the ROM limits. In the preferred embodiment, depending upon which ROM limit is reached, either of the laces is in tension. In an alternative embodiment, the laces from both spools can be wound into the spools. Hence, both laces are kept under tension so that would perform the drop lock function, meaning the elbow has neither flexion nor extension and is locked in one position within 0 to 150 degrees ROM.

Figure 4:
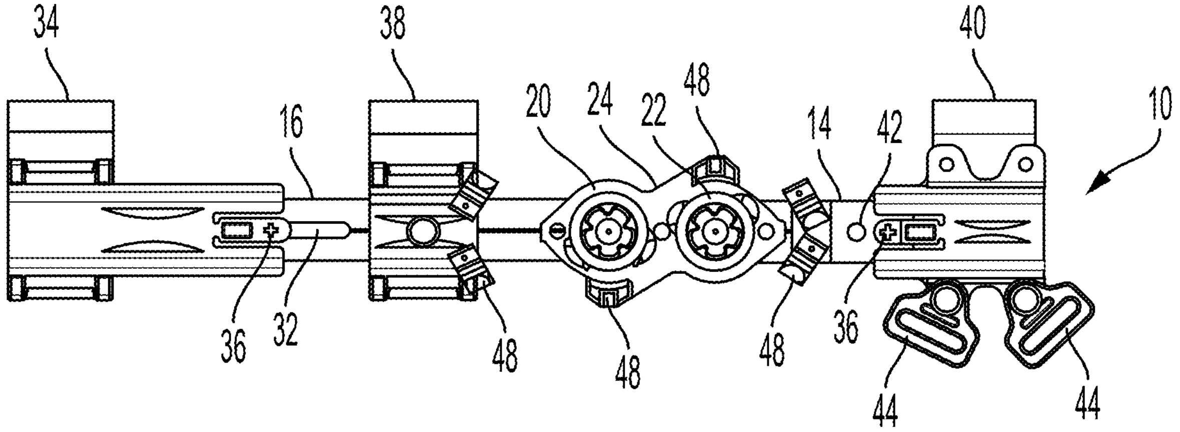
FIG. 4 is a side elevational view of a preferred embodiment elbow brace showing hardware only.
Figure 5:
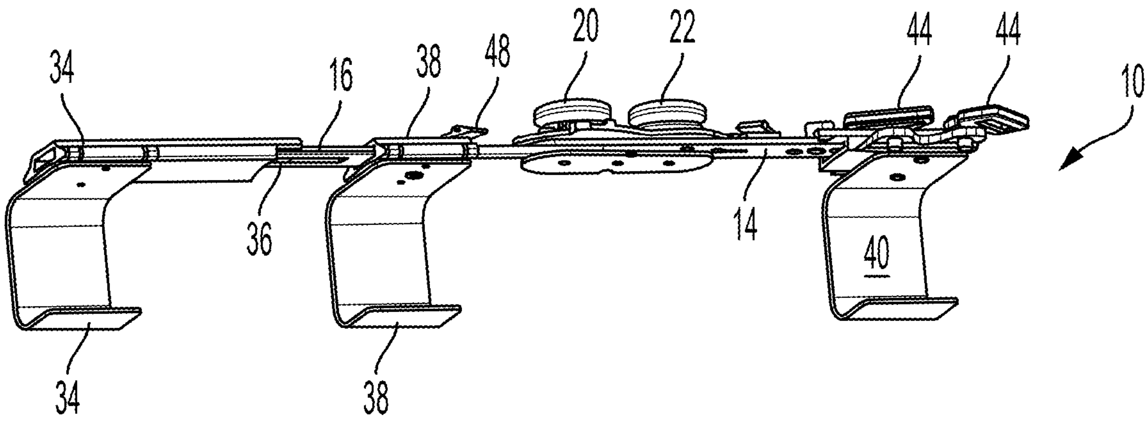
FIG. 5 is a top perspective view a preferred embodiment elbow brace showing hardware only.
Figure 6:
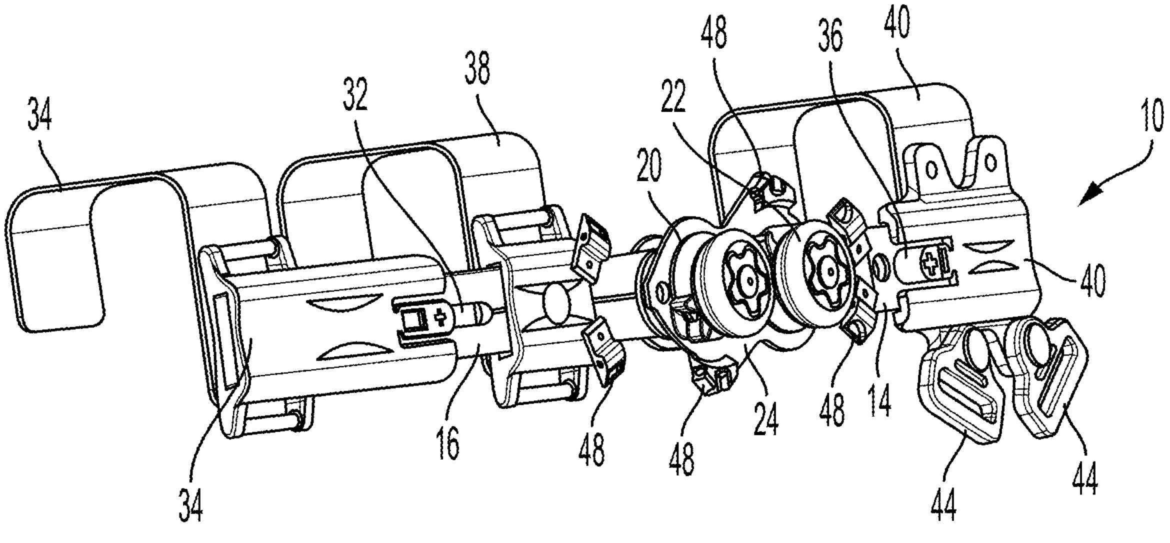
FIG. 6 is another perspective view a preferred embodiment elbow brace showing hardware only.
Figure 7:
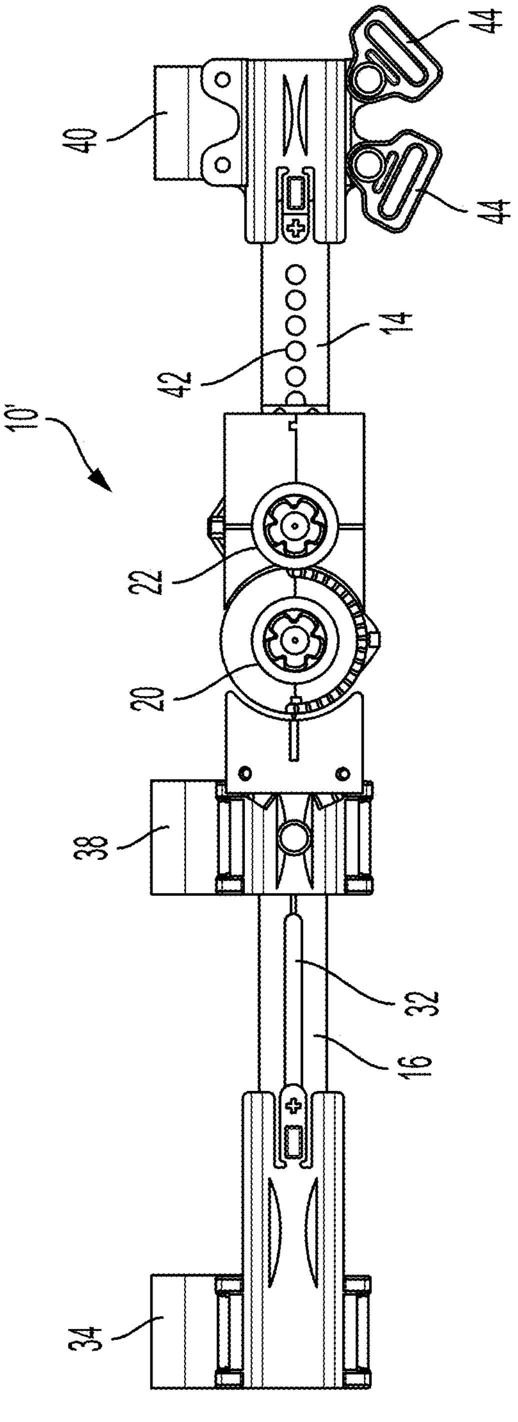
FIG. 7 is a side elevational view of an alternative embodiment elbow brace.

FIGS. 4-6 are various views of the an exemplary embodiment elbow brace 10 showing only the hardware, without the soft goods, fabric covers, padding, etc. FIG. 7 is an alternative embodiment elbow brace 10' with a slightly different spool arrangement. The elbow brace 10 includes a forearm strut 16 and a upper arm strut 14. The struts 14, 16 are preferably fashioned from aluminum, but a rigid polymer, fiberglass, or a combination of metal and plastic and the like are contemplated. The forearm strut 16 includes an elongated slot 32. A first forearm cuff 34 has a mounting bracket with a right angle post or boss 36 that slides along the slot 32, allowing the first forearm cuff 34 to float or slide along the length of the strut 16. Other sliding mechanisms are contemplated, such as parallel rails on the cuff that follow complementary grooves formed in the strut. A second forearm cuff with mounting bracket 38 is preferably attached to the forearm strut 16 via a rivet or boss engaging one or more location holes in the strut, but may be slidably mounted as with the first forearm cuff 34. The first and second forearm cuffs 34, 38 may be independently slidable on the forearm strut 16.

A third cuff with mounting bracket 40 is attached to the upper arm strut 14 and positioned by a post or boss 36 engaging one or more locating holes formed in the strut. The post 36 is preferably a cantilevered or spring biased plunger that hops and locks into any of the plurality of locating holes, depending on the length of the brace needed to properly fit the wearer's limb. Other locking means known in the art are contemplated. The other mounting means described earlier may be applied here.

Any or all of the cuffs may have D-rings formed into the mounting bracket portion of the cuff for attachment straps. In a preferred embodiment, the third cuff 40 engages the humerus/bicep area of the wearer's arm. Attached to the cuff 40 are two optional D-rings 44, that are individually hinged to the cuff, and situated in a (inverted) V-shape arrangement. As seen in FIG. 1, attachment straps 46 are used to hold the D-rings 44 and upper arm strut 14 to the wearer's bicep area. The benefit here is that the hinged D-rings allow the straps 46 attached thereto to splay open into an inverted V to hold to the opposite ends of the bicep. The splayed and hinged straps 46 individually move along with the wearer's arm in flexion or extension and as the bicep flexes and relaxes. This contributes to the free floating nature of the preferred embodiment elbow brace 10 so the elbow brace does not become misaligned on the arm or lose proper attachment, which is a common problem in conventional ROM elbow braces.

Moreover, the preferred embodiment elbow brace 10 relies on only three cuff 34, 38, 40. Specifically, there is only one cuff 40 for the upper arm strut 14, whereas the conventional ROM elbow brace requires two cuffs in the upper arm or humerus region. The present design is advantageous, because, first, the omitted upper arm cuff is not present to otherwise clash with the second upper arm cuff at elbow flexion. Second, after elbow surgery, the surgery incision site is typically located just beneath the bicep where a second cuff would otherwise apply pressure and cause pain. Third, without the second upper arm cuff, there is room for the nurse or technician to apply or change wound dressing at the incision site.

FIGS. 4-6 show the two spools 20, 22 positioned on a base plate 24. The base plate 24 may have lace guides or eyelets 48 for conducting the lace 28, 30 therethrough or anchoring the lace thereon. The guides or eyelets 48 are located on the cuffs and/or on the struts.

Figure 16:
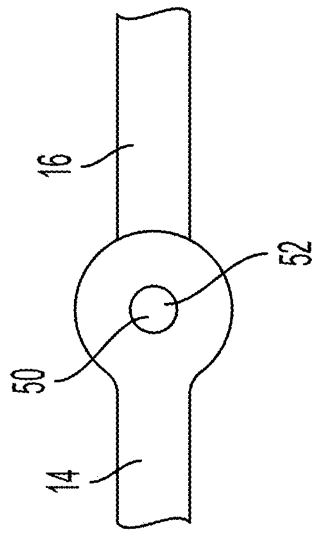
FIG. 16 shows in an exemplary embodiment the upper arm strut hinged to the forearm strut.
Figure 17:
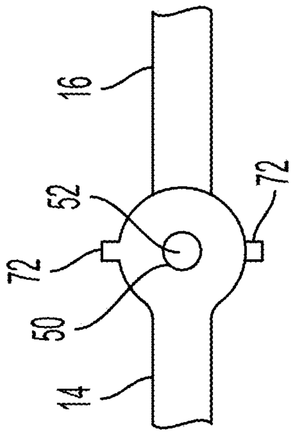
FIG. 17 shows in another exemplary embodiment the upper arm strut hinged to the forearm strut.

FIGS. 16 and 17 show exemplary embodiments of the ends of the forearm strut 16 and upper arm strut 14 include respective pivot points 50. When the pivot points 50 are aligned and a pin 52 is inserted therethough, the struts are able to pivot relative to each other. Other strut pivot mechanisms known in the arm may be used with the present elbow brace.

Figure 18:
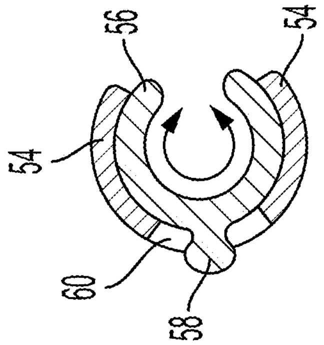
FIG. 18 is a cross-sectional view of a cuff with an internal, axially rotating sleeve with an attachment boss enabling the cuff to rotate relative to the strut.

FIG. 18 shows a cross-sectional end view of an alternative embodiment cuff 54. Inside the cuff is an internal sleeve 56 that engages the wearer's forearm or upper arm. The sleeve 56 has a radial boss 58 that passes through the cuff 54 and is freely slidable within a slot 60 in the cuff 54. This slot 60 enables the boss 58 and sleeve 56 to rotate axially within the cuff 54, as indicated by the arrows. Furthermore, the boss 58 may have a mushroom shape may be used to attach the cuff 54 to a strut, so the cuff is further free to rotate relative to the strut. These features increase the degrees of freedom in rotation for the cuff and improves the ability of the elbow brace closely following the complex arm and elbow movement.

Figure 10:
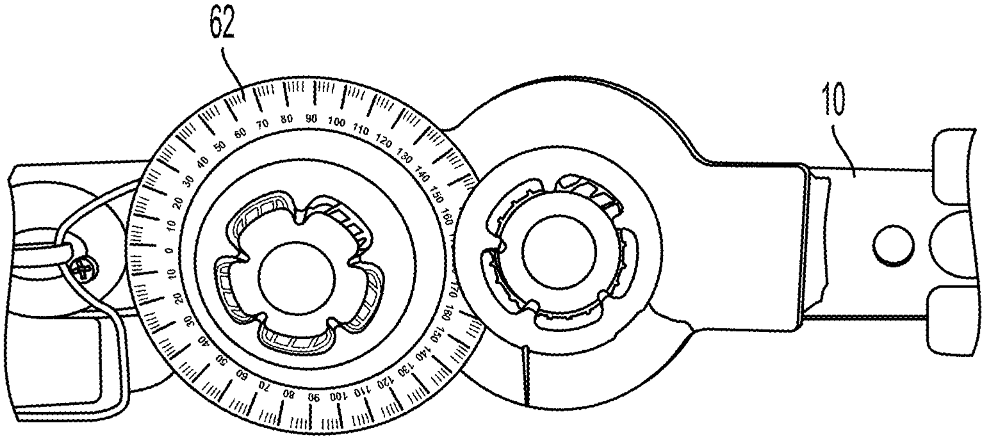
FIG. 10 is an enlarged view of an elbow brace with a goniometer.

Because of this improved fitment of the present invention elbow brace to closely track the wearer's elbow/arm movement through the defined ROM with minimal "slop" or separation of the elbow brace from the arm, it is possible to closely measure the exact ROM limits. A goniometer is a tool that measures an angle or permits the rotation of an object to a definite position. In orthopedics, the goniometer is used in measuring the joint ranges in each plane of the joint, and is often used by a physical therapist to measure a patient's ROM for a limb. FIGS. 1 and 10 show an indicator dial-specially, a goniometer 62-fitted to the elbow brace 10 proximate the hinge pin 52 (FIG. 16); the goniometer 62 may be linked to the struts 14, 16 to measure the ROM angles. A separate goniometer is not needed in many instances for elbow brace 10, because the goniometer is now mounted directly to the elbow brace, which brace closely follows the elbow movement to provide accurate readings.

Figure 8:
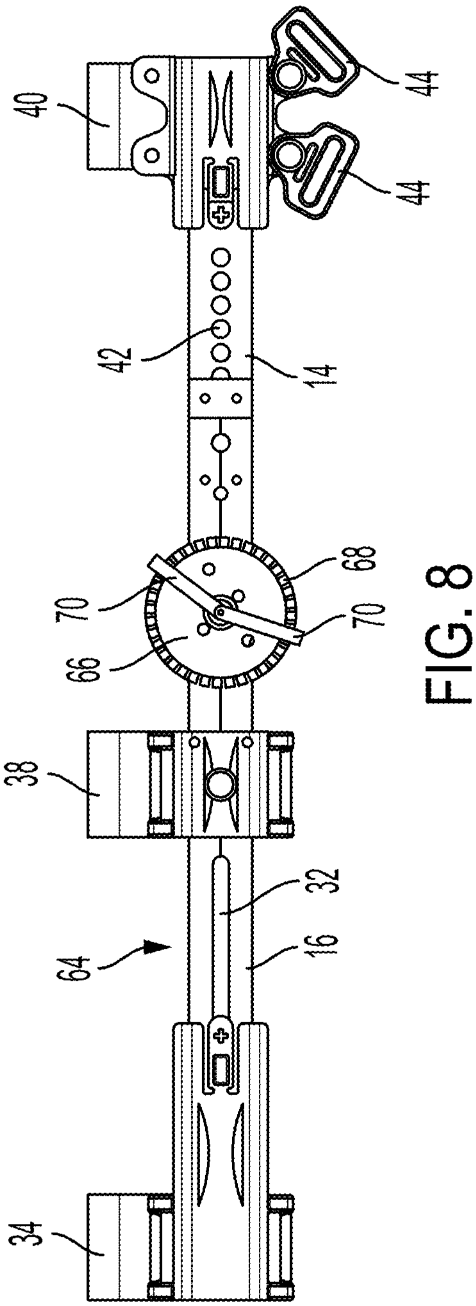
FIG. 8 is a side elevational view of an alternative embodiment elbow brace without using spools and laces.
Figure 9:
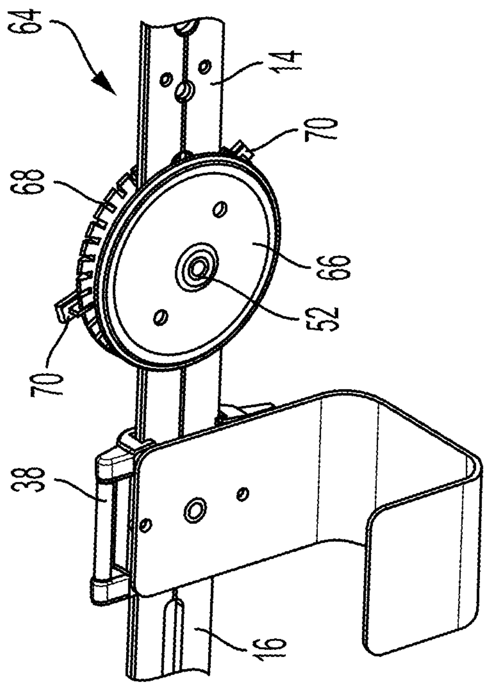
FIG. 9 is a partial perspective view of the interior facing side of the elbow brace from FIG. 8.

FIGS. 8-9 show an alternative embodiment elbow brace 64 which construction is identical to the other embodiments disclosed, but where the spool and laces are replaced by a conventional hinge 66 with ROM limit stops 70. The center hinge 66 has a disc with circumferentially arranged teeth 68. Flexion and extension stops 70 are interposed in the teeth 68 by the physical therapist to set the desired ROM. As seen in FIG. 17, the upper arm strut and forearm strut each has a nub 72 located at a circumference at one end of the strut. The nub 72 for each strut engages the respective stop 70 at the limits of the set ROM. Other types of drop block hinges for setting ROM known in the art can be used here.

Figure 11:
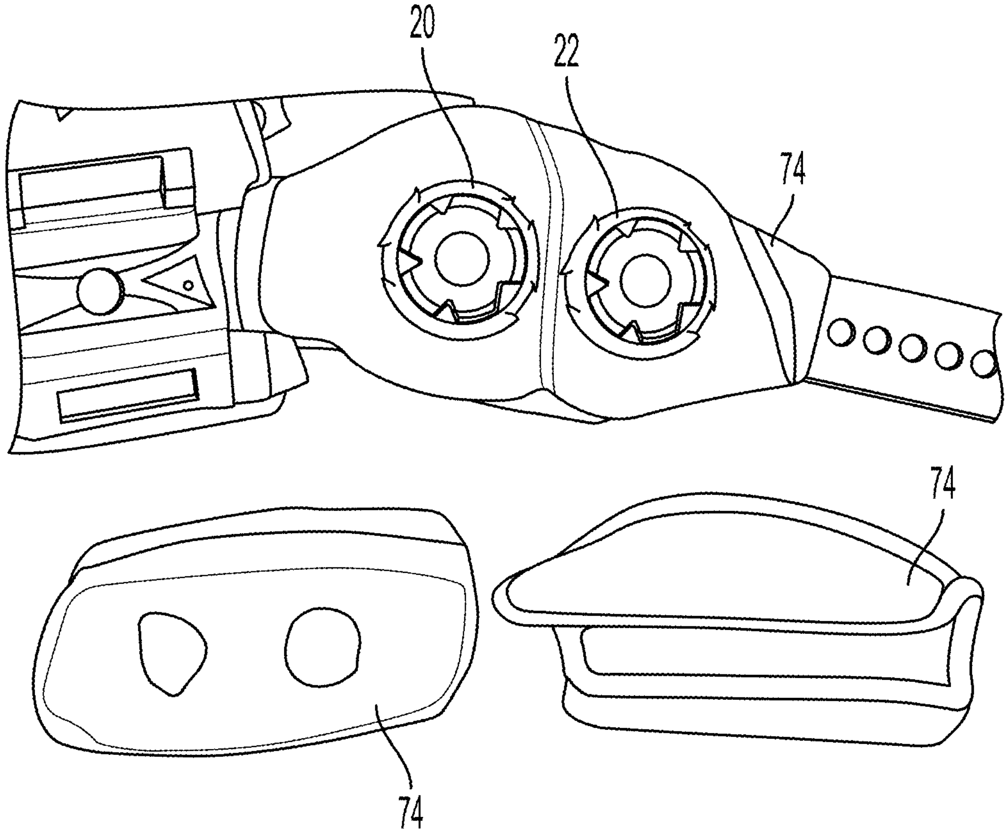
FIG. 11 are three views of the spool and base plate fabric cover.

FIG. 11 presents multiple views of a fabric cover 74 used to enclose the base plate 24 for the two spools 20, 22. Openings in the fabric cover 74 allow the laces to move freely with the rotation of the spools. The fabric includes optional padding to soften the contact with the wearer's arm. The spools 20, 22 are exposed through the fabric cover 74 to allow for access.

Figure 12:
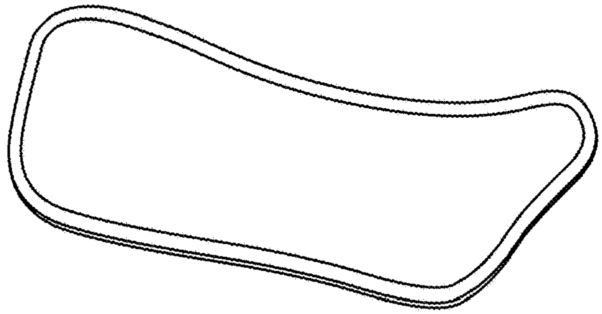
FIG. 12 is a cuff covered with soft goods.
Figure 13:
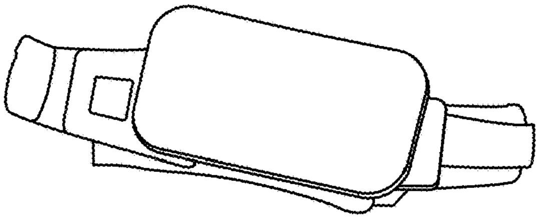
FIG. 13 shows a moldable cuff with a liner pad.
Figure 14:
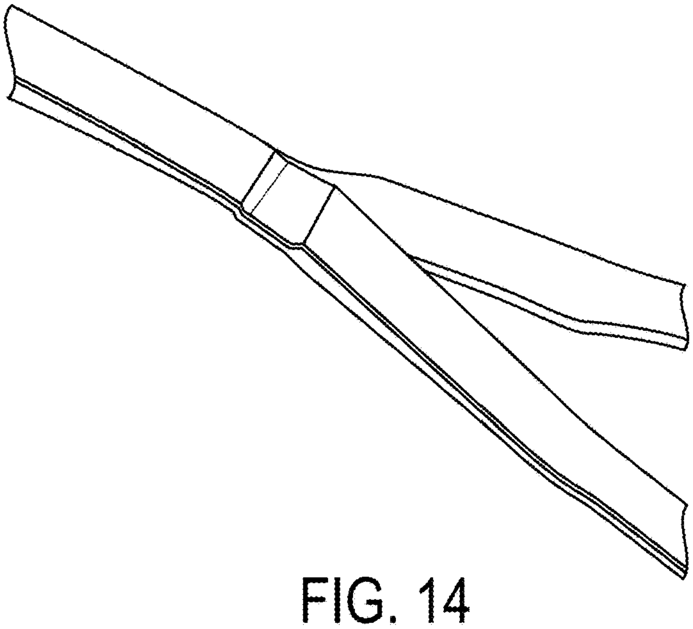
FIG. 14 shows a stretchable V-strap.
Figure 15:
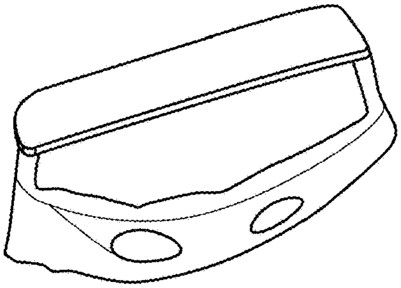
FIG. 15 shows a spool and base plate fabric cover.

FIG. 12 is a preferred embodiment cuff covered by a soft goods shell. The aluminum cuff is made from a pliable, shapeable metal, formed into a U-shape. FIG. 13 shows a moldable aluminum cuff covered by a non-slip silicone coated strap, pad, or liner. FIG. 13 shows a V-strap for uses with the D-rings 44 and elsewhere covered with a non-slip silicone coated strap, pad, or liner. FIG. 15 is another view of the fabric cover 74 for the spool/base plate. The preferred embodiment elbow brace may be further covered with soft goods fabric, gel pads, orthopedic foam and the like at or in the cuffs, struts, etc. to improve comfort.

From the foregoing detailed description, it should be evident that there are a number of changes, adaptations and modifications of the present invention that come within the province of those skilled in the art. Features or structures of one embodiment may be combined with features or structures in another embodiment. However, it is intended that all such variations not departing from the spirit of the invention be considered as within the scope thereof except as limited solely by the following claims.

What is claimed is:

1. An orthopedic elbow brace, comprising:

an elongated forearm strut and an elongated upper arm strut;

a single strut pivot joining the elongated forearm strut and the elongated upper arm strut together;

first and second cuffs disposed on the elongated forearm strut, wherein at least one of the first and second cuffs is slidable along the elongated forearm strut;

a third cuff disposed on the elongated upper arm strut;

at least two pivoting D-rings located proximate to each other for a V-formation and disposed on the third cuff;

first and second rotatable spools disposed on a common base plate wherein the common base plate includes an integral, single-piece plane that does not include a hinge for out-of-plane bending, and the first and second rotatable spools are positioned proximate and acting on the single strut pivot to define a range of motion contained within a single plane that is parallel to the common base plate;

a first lace interconnecting at least one of the elongated forearm strut and the elongated upper arm strut to the first rotatable spool, and a second lace interconnecting at least one of the elongated forearm strut and the elongated upper arm strut to the second rotatable spool, wherein rotating the first and second rotatable spools tensions the first and second laces to set an angular position between the elongated forearm strut and the elongated upper arm strut in flexion and in extension, corresponding to the range of motion contained within the single plane, and wherein the elongated forearm strut and the elongated upper arm strut move within the range of motion contained within the single plane in use; and a plurality of straps disposed on the at least two pivoting D-rings and on the first and second cuffs.

2. The orthopedic elbow brace of claim 1, wherein the first lace wraps around the first rotatable spool and interconnects with the elongated forearm strut, and the second lace wraps around the second rotatable spool and interconnects with the elongated upper arm strut.

3. The orthopedic elbow brace of claim 1, wherein the first lace wraps around the first rotatable spool and interconnects with the elongated forearm strut and the elongated upper arm strut, and the second lace wraps around the second rotatable spool and interconnects with the elongated forearm strut and the elongated upper arm strut.

4. The orthopedic elbow brace of claim 1, wherein the elongated forearm strut includes a longitudinal slot and at least one of the first and second cuffs includes a post freely slidable therein.

5. The orthopedic elbow brace of claim 1, wherein the orthopedic elbow brace includes a goniometer disposed proximate the strut pivot.

6. The orthopedic elbow brace of claim 1, wherein at least one of the first, second, and third cuffs includes an internal sleeve that rotates axially.

* * * * *